US006531577B1

(12) United States Patent
Kaersgaard et al.

(10) Patent No.: US 6,531,577 B1
(45) Date of Patent: Mar. 11, 2003

(54) VON WILLEBRAND FACTOR (VWF)-CONTAINING PREPARATION, PROCESS FOR PREPARING VWF-CONTAINING PREPARATIONS, AND USE OF SUCH PREPARATIONS

(75) Inventors: Per Kaersgaard, Naerum (DK); Karina Alsoe Barington, Virum (DK)

(73) Assignee: Hemasure Denmark A/S, Gentofte (DK)

(*) Notice: Subject to any disclaimer, the term of this patent is extended or adjusted under 35 U.S.C. 154(b) by 0 days.

(21) Appl. No.: 09/210,338

(22) Filed: Dec. 11, 1998

(30) Foreign Application Priority Data

Dec. 15, 1997 (DK) ................................................ 1459/97

(51) Int. Cl.$^7$ ............................................. C07K 17/745
(52) U.S. Cl. ........................ 530/381; 530/380; 530/382; 530/383; 530/384; 514/12
(58) Field of Search .......................... 530/380, 381, 530/382, 383, 384; 514/12

(56) References Cited

U.S. PATENT DOCUMENTS

| 5,854,403 A | 12/1998 | Fischer et al. ............... 530/412 |
| 5,869,617 A | 2/1999 | Fischer et al. ............... 530/381 |
| 5,877,152 A | * 3/1999 | Fischer ........................ 514/12 |
| 6,005,077 A | * 12/1999 | Schwartz ..................... 530/383 |
| 6,228,613 B1 | 5/2001 | Fischer et al. ............. 435/69.1 |

FOREIGN PATENT DOCUMENTS

| EP | 469 985 B1 | * 4/1997 |
| WO | WO 91/07438 | * 5/1991 |

OTHER PUBLICATIONS

Lynch, Annals NY Acad Sci 614, 138–152, 1991.*
Furlan, Annals of Hematoglogy 72, 341,1996.*
McLellan Medical Laboratory Sciences 45, 358–369, 1988.*
Barington, Vox Sanguinis 76, 85–89, 1999.*
Hornsey, Thrombosis and Haemostasis 57, 102–105, 1987.*
Burnouf–Radosevich, Vox Sang 62, 1–11, 1992.*
Rodeghiero et al., Vox Sang. 62, 193–199 (1992).*
Mannucci et al., Haemostasis 24, 285–288, 1994.*
Mannucci et al., Blood 83(10), 3018–3027 (1994).*
Ruggeri and Ware, Faseb J. 7, 308–316, 1993.*
Ruggeri and Zimmermann, Blood 57(6), 1140–1143, 1981.*
Prince et al. The Lancet, 706–710, Mar. 29, (1986).*
Hart et al. Vox Sanguinis 67, 345–350 (1994).*

* cited by examiner

Primary Examiner—Christopher S. F. Low
Assistant Examiner—David Lukton
(74) Attorney, Agent, or Firm—Darby & Darby (57) ABSTRACT

A high-purity von Willebrand factor preparation, a process for making it, and use of the preparation and compositions containing it for the treatment of disorders are disclosed.

9 Claims, 2 Drawing Sheets

VON WILLEBRAND FACTOR (VWF)-CONTAINING PREPARATION, PROCESS FOR PREPARING VWF-CONTAINING PREPARATIONS, AND USE OF SUCH PREPARATIONS

FIELD OF THE INVENTION

The present invention relates to a high-purity von Willebrand factor (vWF) preparation as well as to a process for making such preparation. The invention further relates to the use of such preparation for the treatment of bleeding disorders and to a pharmaceutical composition comprising such preparation and suitable for treating these disorders. In a further aspect, the present invention relates to a method for treating bleeding disorders. The bleeding disorder may suitably be von Willebrand's Disease (vWD), haemophilia A induced by vWF-dependent FVIII deficiency or haemophilia A not induced by such deficiency.

BACKGROUND OF THE INVENTION vWF is an adhesive glycoprotein synthesised by megakaryocytes and endothelial cells. vWF circulates in plasma as an array of multimers of increasing size, from the protomers of approximately 500 kD to the largest multimers having a molecular weight of approximately 20,000 kD. Each protomer of 500 kD is made up of two identical monomeric subunits and is therefore also referred to as dimer. The multimers are made up of repeating units of protomers. vWF plays an important role in normal haemostasis due to two main functions. Firstly, vWF is essential to coagulation due to its ability to serve as a carrier of coagulation factor VIII (FVIII), which is a plasma protein that participates in the intrinsic pathway of blood coagulation. The formation of such complexes protects FVIII from proteolytic inactivation. Secondly, vWF contributes, through different mechanisms, to platelet adhesion and aggregation.

Disturbances in blood plasma level of vWF and/or FVIII lead to very serious, sometimes life-threatening, bleeding disorders.

von Willebrand's Disease (vWD) is an autosomal inherited bleeding disorder, the onset of which is due to deficiency and/or abnormality of vWF. As a consequence, FVIII coagulant activity (FVIII:C) is often reduced, since, as mentioned above, vWF serves as a carrier of FVIII. The relevance of vWF for platelet adhesion to the damaged endothelium is reflected by the fact that patients with vWD also often have prolonged skin bleeding time.

vWD is the most common inherited bleeding disorder. It has been demonstrated that its prevalence in the general population is at least 0.8%, and a multiethnic paediatric survey (made in 1993) in the US has given a figure of 1.3%, confirming that the disease has no racial differences and is distributed world-wide.

Epistaxis, bleeding after dental extraction and menorrhagia are the most prominent symptoms, being present in about 60% of the affected patients. Often, bleeding symptoms lessen with age in patients with a mild form of the disease. Epistaxis is very frequent during childhood. Menorrhagia is the most frequent clinical problem in women with vWD, often requiring the combination of oral contraceptive pill and iron supplementation. In patients with classical vWF deficiencies, postpartum bleeding is not often encountered since vWF level usually increases during pregnancy, whereas patients with the variant forms usually require peripartum replacement therapy. Patients with severe disease may experience muscular or joint bleeding because of the concomitant markedly reduced FVIII levels. Furthermore, bleeding after surgery may be life-threatening.

Three main types of vWD have been identified. Type 1, with classical autosomal dominant inheritance, accounting for about 70% to 80% of cases, is characterised by equally low FVIII/vWF measurement, with no evidence of structural abnormality on multimeric analysis. Type 2 is usually characterised by the lack of large multimers and abnormally low levels of vWF:RCo in comparison with VWF:Ag. In this group, several subtypes, sometimes with recessive inheritance, have been observed. The phenotypes of type 2 is classified as A (patients with the absence of high molecular weight vWF-multimers and decreased platelet-dependent function), B (patients with hyperresponsiveness to ristocetin), M (patients with qualitative variants with decreased platelet-dependent function but with high molecular weight multimers present) and N (patients with defective FVIII-VWF binding). Type 3 is recessively transmitted and patients have very low or undetectable levels in all FVIII/vWF measurements.

vWF deficiency may also lead to phenotypical haemophilia A as vWF is essential for the function of FVIII. In these cases, the half-life of FVIII is decreased. Thus, patients suffering from vWD do often also suffer from FVIII deficiency. The reduced FVIII activity is not a result of a gene defect, but rather an indirect consequence of the vWF deviation. Normally, decreased ristocetin-cofactor activity and vWF antigen level are observed in vWD patients, whereas this is not the case in haemophilia A patients.

Haemophilia A is caused by partial or complete lack of the important coagulation protein FVIII, which circulates in the plasma completed with vWF, in the patient's blood. The disease is inherited in a X-chromosome recessive pattern, and therefore it mainly affects males, but heterozygous females are asymptomatic carriers of the disease. The FVIII gene has been located to the long arm of the X-chromosome.

The coagulation process is an enzymatic cascade reaction enrolling intricate feedback activating and inactivating mechanisms. Most of the activated enzymes of the cascade require co-factors to be efficient, and some of these co-factors are plasma proteins which exist in both an active and an inactive form. Coagulation FVIII is one of such co-factors. In haemophilia A patients, a delayed clot formation is observed leading to excessive bleeding and poor wound healing. Haemorrhagic episodes in patients with haemophilia A can be managed by substituting FVIII.

The main symptoms of haemophilia A are excessive and prolonged bleeding. In severe haemophilia (less than 1% FVIII present), the most common sites of bleeding are in the large joints of the limps and in the large muscles. Unless such bleeding is controlled promptly by infusion of FVIII, the main chronic complications of haemophilia, namely arthropathy and muscle atrophy will occur. In mild haemophilia A (5–40% FVIII present), bleeding usually does not occur except after trauma. Moderately severe haemophilia A (1–5% FVIII present) has clinical features in between severe and mild haemophilia A and may show the largest individual variation.

In vWD, the main goal of treatment is to correct the bleeding time and FVIII defects. This is conventionally accomplished by administering the synthetic drug desmopressin (DDAVP) or by replacement therapy with FVIII/vWF preparations.

However, some patients with vWD do not respond to DDAVP treatment. Furthermore, patients initially responsive to DDAVP treatment may become refractory, when repeated infusions are given to maintain hemostasis over long periods of time. In these situations, the most commonly used treatment is replacement therapy with blood products such as cryoprecipitates or other concentrates prepared from plasma.

Cryoprecipitates are vWF-rich preparations obtained by thawing frozen blood plasma to 2–4° C. and isolating the non-dissolved fraction. However, treatment with cryoprecipitates has been shown not to be sufficiently effective as correction of the bleeding time was only obtained in 24% of the cases, only partially in 36% of the cases, whereas no effect was observed in 40% of the cases (see Ref. 1). Furthermore, there is a high risk of transmitting life-threatening blood-borne viruses such as HIV and hepatitis viruses since virucidal methods cannot be applied directly to the cryoprecipitates normally used. Another disadvantage is the high content of fibrinogen and anti-A and anti-B agglutinins in these preparations, the presence of which may lead to hyper-fibrinogenaemia and anaphylactic reactions in patients with blood types A or B. Furthermore, due to the low concentration of vWF in this type of preparations, large volumes of fluid must be infused, and repeated infusions over time entail exposure to a large number of different donors thereby increasing the risk of infection with blood-borne viruses. These facts render the use of cryoprecipitates unsuitable for treating vWD.

In spite of the above-mentioned limitations, cryoprecipitates have been used in the treatment of patients suffering from haemophilia A. To avoid the above-mentioned problems, concentrates of FVIII, which are virus inactivated, have been developed. However, as the quality and safety of such concentrates have increased, the content and quality of vWF have diminished. High amounts of vWF are often present in low purity concentrates, whereas the content is low in medium and high-purity FVIII concentrates. In very high-purity concentrates such as affinity purified concentrates, vWF is almost absent. Thus, most high- and very high-purity concentrates are not suitable for treatment of vWD patients, whereas the low-purity concentrates contain high amounts of fibrinogen and high anti-A and anti-B agglutinin titres, thus entailing the above-mentioned disadvantages.

It has been found that a high content of high-molecular weight vWF (HMW-vWF)-multimers is essential for the effectiveness of the vWF preparation. Conventionally used preparations lack such HMW-vWF-multimers. This could be due to the presence of platelet proteases degrading the HMW-multimers during fractionation. As described in U.S. pat. No. 4,710,381 A (Ref. 2), it is important removing blood platelets from plasma intended for fractionation thereby hindering calcium-activated protease(s) present in blood platelets from being released and cause degradation of vWF, or, alternatively, adding calcium-chelating agents during fractionation thereby hindering released protease(s) from being calcium-activated.

A marked degree of vWF-fragmentation has been demonstrated in cryoprecipitates prepared from pooled plasmapheresis plasma, which is the starting fraction for producing most commercial concentrates (see Ref. 3 and Ref. 4). The vWF-degradation was shown to be proportional to the number of platelets present in the starting plasma. The degradation could be greatly diminished when collecting plasma in the presence of protease inhibitors (e.g. EDTA). On the basis of these findings, it was concluded that the loss of HMW-multimers resulted from the use of large plasma pools containing units of poorly centrifuged (plasmapheresis) plasma with an excessive number of residual platelets and leukocytes, lysing and liberating vWF-degrading proteases when the plasma is frozen and thawed. It was further concluded that vWF-preparations which had an intact HMW-vWF-multimeric pattern could not be prepared from pooled plasma containing poorly centrifuged plasmapheresis or whole blood plasma which had been frozen (see Ref. 3 and 4).

As outlined above, the known purification procedures result in loss of essential HMW-multimers. As none of the currently available preparations are, at the same time, sufficiently effective, pure and virus safe, there is a strong need for a preparation which at the same time is safe for the patient, effective, easily prepared and economically feasible.

These goals are fulfilled by the preparation of the present invention.

DESCRIPTION OF PRIOR ART

In EP 469 985 B1 (Ref. 5), a process for manufacturing vWF of high purity, largely devoid of FVIII:C is disclosed, which process comprises purification by ion exchange chromatography using a first chromatography column onto which FVIII:C is adsorbed. The non-retained fraction which contains the vWF is then treated so as to decrease the ionic strength, and the vWF fraction is then subjected to ion exchange chromatography, whereby vWF is adsorbed onto the gel of a second column with a first elution solution and then desorbed using a second elution solution of higher ionic strength than the first elution solution yielding the high purity vWF product. The second ion change chromatography is performed using a gel for exchanging anionic type ions. The crude solution containing FVIII:C as well as vWF may be subjected to diafiltration prior to the first purification step. In EP 469 985 B1, it has not been suggested to use gel filtration nor to use cation exchange chromatography for purification.

In WO 91/07438 A1 (Ref. 6), a method for isolating FVIII from other proteins using gel filtration is described. The gel filtration medium is constituted of particles being inert to FVIII. The method has not been used for preparing vWF preparations.

EP 705 846 A1 (Ref. 7), WO 96/10584 A1 (Ref. 8) and WO 97/34790 A1 (Ref. 9), respectively, describe methods for purifying vWF or the FVIII:C/vWF complex using anion exchange chromatography and affinity chromatography on immobilised heparin. High purity vWF products are obtained from both plasma-derived starting materials and cell supernatants containing recombinant vWF. The content of fibrinogen and fibronectin has not been measured or specified in any of the vWF products, and the multimeric structure has not been characterised using agarose gels that are suitable for separating HMW-multimers composed of 13 or more promoters. Furthermore, the gel electrophoresis methods used for evaluating the structural integrity of the vWF-multimers indicate that the products have a very low content of such HMW-multimers.

In EP 705 846 A1, a process for separating vWF into HMW-vWF and LMW-vWF is described, by which process vWF is bound to immobilised heparin, and the HMW-vWF and LMW-VWF are eluted at different salt concentrations. The affinity chromatography on immobilised heparin may be carried out at pH 6.0% to 8.5, preferably at pH 7.4. The HMW-VWF is eluted at a higher salt concentration than the salt concentration used for eluting LMW-vWF. Furthermore, a HMW-vWF fraction and a LMW-VWF fraction are claimed. Whereas the LMW-vWF fraction is claimed to contain at least 83% dimers, at maximum 16% tetramers and at maximum 1% other multimers, no such claims have been made in the case of the HMW-vWF fraction. A characterisation of the multimeric structure of a recombinant HMW-vWF fraction obtained by the process shows that the content of multimers composed of 13 or more protomers is less than 1%. The platelet aggregation activity of the fraction is specified to be at least 50% improved compared to the activity of vWF in the mixture of LMW-vWF and HMW-VWF. In Examples 5 and 6, recombinant vWF is purified using a combination of anion exchange chromatography and affinity chromatography using immobilised heparin.

In WO 96/10584 A1, a process for extracting high-purity vWF is described, whereby recombinant vWF is subjected to anion exchange chromatography using a quaternary amino-type anion exchanger. The-recombinant vWF is bound at a salt concentration below 270 mM and eluted at a salt concentration above 270 mM. The so obtained fraction is preferably purified further using affinity chromatography on immobilised heparin. Again, the obtained vWF has not been characterised as it is only stated that the vWF fraction contains multimers having a high structural integrity.

From WO 97/34930 A1, a stabile FVIII/vWF-complex is known, which complex contains HMW-vWF-multimets and which further does not contain LMW-VWF molecules and proteolytic vWF decomposition products. It is further stated that the complex has a specific platelet agglutination activity of at least 50 IU/mg vWF:Ag. The FVIII/vWF complex is obtained using affinity chromatography on immobilised heparin, and the high stability is obtained by introducing a washing buffer containing 10 mM $CaCl_2$ during the anion exchange step. This washing step ensures the removal of proteolytic vWF decomposition products as well as some proteolytic proteins. Again, the multimeric structure has not been characterised using suitable agarose gels able to separate HMW-multimers composed of 13 or more protomers, but the gel electrophoresis methods used for evaluating the structural integrity of the vWF-multimers indicate that the products have a very low content of such multimers.

SUMMARY OF THE INVENTION

In accordance with the claims, the present invention relates to a vWF preparation comprising HMW-vWF-multimers, a process for preparing vWF-containing preparations as well as to the use of such preparations for preparing a medicament for the treatment of bleeding disorders. Furthermore, the invention relates to a pharmaceutical composition comprising said preparation and to a method for treating bleeding disorders.

Thus, in the broadest aspect, the present invention relates to a high-purity vWF-containing preparation, comprising at least 15% vWF-multimers composed of 13 or more protomers calculated on the basis of the total content of vWF-multimers and further having a low content of fibrinogen and fibronectin.

The following abbreviations are used throughout the present context.

| vWF | von Willebrand factor (important haemostatic protein and stabiliser of FVIII) |
| --- | --- |
| vWF:Ag | von Willebrand factor antigen (the amount of vWF protein as determined by an ELISA assay) |
| vWF:CBA | von Willebrand factor collagen binding activity (the haemostatic activity of vWF determined as the ability of vWF to bind to collagen in an ELISA assay) |
| vWF:RCo | ristocetin co-factor activity |
| FVIII | factor VIII coagulation factor (a coagulation factor associated to vWF) |
| FVIII:C | FVIII procoagulant activity |
| ELISA | enzyme-linked immunosorbent assay |

As used herein, the term "LMW (low molecular weight)-vWF mulitimers" is intended to mean multimers composed of one to six protomers and having a molecular weight of from approximately 500 kD to approximately 3,000 kD, the term "IMW (intermediate molecular weight)-vWF-multimers" is intended to mean multimers composed of seven protomers to twelve protomers and having a molecular weight of from approximately 3,500 kD to approximately 6,000 kD, and the term "HMW (high molecular weight)-vWF-multimers" is intended to mean multimers composed of thirteen or more protomers and having a molecular weight of approximately 6,500 kD and higher.

It is a generally accepted fact that purification of a vWF-containing preparation having intact HMW-multimeric pattern and being prepared from pooled frozen plasmapheresis plasma cannot be obtained without, at the same time, the use of protease inhibitors being required. In accordance with the present invention, it has been demonstrated that a high-purity vWF-containing preparation containing practically all the HMW-vWF-multimers present in plasma can, surprisingly, be produced from normal pooled plasma, in particular from plasmapheresis plasma, without rendering necessary the use of protease inhibitors. The preparations can furthermore be prepared from plasma, which has been frozen and thawed.

High-purity plasma preparations are often combined with the stabilising protein human serum albumin which is regarded as completely safe and harmless. However, addition of albumin does give rise to difficulties in assessing the purity or specific activity of a preparation as the specific activity is traditionally expressed as the content of the active ingredient (e.g. vWF) relative to the total protein content. Thus, the total amount of quantitated protein in albumin-stabilised preparations will include the co-purified contaminants of concern as well as added albumin stabiliser.

The specific activity of a preparation should be assessed relative to specific contaminating proteins like fibrinogen and fibronectin. In most FVIII/vWF-preparations, fibrinogen and fibronectin are the main contaminating substances due to their cold-insoluble characteristics because of which they are precipitated and collected together with FVIII/vWF during cryoprecipitation which as earlier stated is the initial step of traditional plasma fractionation.

The result obtained by vWF-multimer analyses depends very much on the exact assay conditions, especially the percentage of agarose present in the gel matrix. Thus, the presence or absence of HMW-vWF-multimers can only be determined in gels of low agarose concentration (see Ref. 10). Accordingly, if the vWF-multimer analysis gel matrix contains acrylamide, it is important to keep the acrylamide concentration low when detecting HMW-vWF-multimers. Ruggeri and Zimmerman (see Ref. 11) showed that HMW-vWF-multimers cannot enter gels consisting of 2.5% acrylamide and 0.8% agarose or gels consisting of 3.0% acrylamide and 0.5% agarose, and are therefore not detectable in these gels whereas they do enter gels consisting of 0.8% agarose and 1.75% acrylamide. If this important impact of the gel composition on the vWF-multimer assessment is not considered, conflicting conclusions of vWF-multimer analyses might be drawn.

Accordingly, only low agarose and acrylamide concentrations in the gels are suitable for detecting HMW-vWF-multimers as positive vWF-multimer results obtained in higher concentration gels might be incorrect. Therefore, the analysis conditions (especially the gel composition) used for detecting HMW-vWF-multimers need to be specified in order to evaluate and compare results obtained.

DETAILED DESCRIPTION OF THE INVENTION

In one aspect, the present invention relates to a high-purity vWF-containing preparation, comprising at least 15% vWF-multimers composed of 13 or more protomers calculated on the basis of the total content of vWF-multimers and further having a low content of fibrinogen and fibronectin. A preparation comprising practically all blood plasma HMW-vWF-multimers as demonstrated by the low agarose concentration vWF-multimer analysis described below in Example 1 can surprisingly be obtained. As HMW-vWF-multimers are the haemostatically most important vWF-multimers, this high-purity vWF-containing preparation is superior in treating patients suffering from vWD as compared to existing high-purity FVIII-preparations having a lower content of or containing partially degraded vWF-multimers.

The content of HMW-vWF-multimers is calculated on the basis of multimers composed of one or more protomers and having a molecular weight of 500 kD and higher and is determined as described in Example 1.

In one embodiment, the total content of fibrinogen and fibronectin in the preparation is less than 1500 ng/IU vWF.

In a preferred embodiment, the vWF-containing preparation according to the invention comprises at least 18% vWF-multimers composed of 13 or more protomers (HMW-vWF-multimers).

In another embodiment, the amount of fibrinogen is less than 500 ng/IU vWF, preferably less than 200 ng/IU vWF. In another embodiment, the amount of fibronectin is less than 500 ng/IU vWF.

In a further embodiment, the invention relates to a preparation comprising vWF, fibrinogen and fibronectin as indicated above and further comprising more than 0.1 IU FVIII:C/IU vWF, preferably from 0.1% to 3 IU FVIII:C/IU vWF, and most preferably from 0.2% to 1 IU FVIII/IU vWF. The preparations according to the invention are suitable for treating vWD, haemophilia A and haemophilia A caused by vWD-induced FVIII deficiency. In a preferred embodiment, the vWF preparations are prepared from human plasma, although the preparations may also be obtained from solutions containing recombinantly prepared vWF.

In another aspect, the present invention relates to a process for preparing a vWF-containing preparation which process comprises the steps of performing an anion exchange chromatography of a first vWF-containing solution whereby vWF is adsorbed, and subsequently desorbing vWF using a first elution buffer of higher ionic strength than the first vWF-containing solution, collecting the vWF-containing eluate, adjusting the ionic strength of said vWF-containing eluate, thereby obtaining a second vWF-containing solution of lower ionic strength than said eluate, and performing a cation exchange chromatography, whereby vWF is adsorbed, and subsequently desorbing vWF using a second elution buffer of higher ionic strength than the ionic strength of the second vWF-containing solution, and collecting the vWF-containing eluate, or performing a cation exchange chromatography of a first vWF-containing solution whereby vWF is adsorbed, and subsequently desorbing vWF using a first elution buffer of higher ionic strength than the first vWF-containing solution, collecting the vWF-containing eluate, adjusting ionic strength of said vWF-containing eluate, thereby obtaining a second vWF-containing solution of lower ionic strength than said eluate, and performing an anion exchange chromatography, whereby vWF is adsorbed, and subsequently desorbing vWF using a second elution buffer of higher ionic strength than the ionic strength of the second vWF-containing solution, and collecting the vWF-containing eluate.

It is to be understood that anion exchange chromatography may be performed firstly, or cation exchange chromatography may be performed firstly. In a preferred embodiment, anion exchange chromatography is performed firstly, and cation exchange chromatography is performed subsequently.

The buffers used in the two steps may be the same or different.

In a preferred embodiment, the anion exchange chromatography and the cation exchange chromatography are performed under substantially the same conditions.

In one embodiment, the anion exchange chromatography is performed at pH 6% to pH 8.5, and the cation exchange chromatography is performed at pH 6% to pH 8.5.

As anion exchanger, Q-Sepharose® or DEAE-Fractogel® may suitably be used. As cation exchanger, SP-Sepharose® may suitably be used. As elution buffer, any buffer normally used in connection with chromatography may suitably be used. Examples are Tris, citrate, histidine, lysine and acetate buffers.

It has surprisingly been found that the preparations of the invention can be obtained by performing two ion exchange chromatography steps, i.e. an anion exchange chromatography step and a cation exchange chromatography step. The chromatography steps may preferably be performed under substantially the same conditions. It has surprisingly been found that this leads to a very high purity of the obtained vWF-containing preparation.

Ion exchange chromatography is a high resolution technique which separates biomolecules on the basis of their charge properties. Since most biomolecules, such as proteins, consist of charged subunits e.g. amino acids and saccharides, ion exchange chromatography is a well-known and widely used technique for purification of proteins. An ion exchanger consists of an insoluble porous matrix to which charged groups have been covalently bound. The charged groups are associated with mobile counter-ions. These counter ions (e.g. salts) can be reversibly exchanged with other ions of the same charge without altering the matrix. Exchangers are available as positively and negatively charged exchangers. Positively charged exchangers have negatively charged counter-ions (anions) available for exchange and are accordingly termed anion exchangers. Negatively charged exchangers have positively charged counter-ions (cations) and are thus termed cation exchangers. A protein with a net negative charge becomes bound to the positive charged groups on the chromatography matrix of an anion exchanger, whereas proteins with a net positive charge do not become bound and run through the column. The opposite conditions are applicable in the case of the cation exchange chromatography step, as proteins with a net positive charge become bound to the negative charged groups on the matrix, and proteins with a net negative charge run through the column. The net charge of a protein depends on the pH of the buffer in which the protein is dissolved. Thus the net charge can be varied by adjusting the pH of the buffer and will decide if the protein has affinity for an anion exchanger or a cation exchanger.

The binding strength of the proteins is also influenced by the ionic strength of the buffer. At low ionic strengths, competition for charged groups on the ion exchanger is at minimum and proteins of opposite charge are bound strongly. Increasing the ionic strength increases competition and reduces the interaction between the ion exchanger and the protein, resulting in their release from the matrix, the most weakly bound proteins being released from the matrix firstly. The ionic strength in the buffer is adjusted by varying the salt concentration.

From the above, it can be understood that the pH and ionic strength of the buffer, used during ion exchange, determines whether a protein become bound to either an anion exchanger or to a cation exchanger.

From the above described, it is thus very surprising that the vWF-containing preparation can be bound to both an anion exchanger and a cation exchanger at substantially the same pH and ionic strength. Furthermore, it has been shown that proteins binding to an anion exchanger together with the vWF-containing preparation, do not become bound to a cation exchanger, when substantially the same pH and ionic strength are used during both steps. The use of both an anion exchange step and a cation exchange step at almost identical pH and ionic strength in the purification of the VWF-containing preparation, therefore, gives a very powerful purification technique that normally is seen only by using e.g. affinity chromatography with monoclonal antibodies. The fact that the vWF-containing preparation becomes bound to an anion exchanger and a cation exchanger under substantially the same conditions does probably relate to the size of the complex, making the existence of large areas with different net charge probable. Also, it seems as if the FVIII-part of the complex has the highest affinity for the anion exchanger, whereas the vWF-part of the complex has the highest affinity for the cation exchanger. The use of both an anion exchanger and a cation exchanger exploits this, when vWF and FVIII are purified together.

The content of FVIII relative to vWF can be varied by changing the composition of the buffers used for ion exchange chromatography, particularly during anion exchange chromatography.

In a preferred embodiment, the process further comprises an initial gel filtration step. Such gel filtration can suitably be performed as described in WO 91/07438, in two different manners, namely group separation mode or fractionation mode.

In the group separation mode, the solutes are separated in the two groups having great differences in their molecular sizes, one group being eluted with the void volume and the other group being eluted later with a much larger elution volume often close to the total "bed volume". This procedure is primarily used to separate proteins from dissolved salts or to exchange buffer and is referred to as "desalting". For "desalting" rigid gels having a small pore size is used and the process may be carried out using large amounts of material (sample volumes constituting 20–30% of the bed volume) and using a high flow rate (about one bed volume of buffer per hour). Thus, the capacity of the column is large.

In the fractionation mode, the solutes having similar molecular weight are separated. This procedure is often used to separate proteins. For this purpose, gel particles having larger pores are used and the gel filtration medium is chosen so as to ensure that the proteins are eluted more closely than when using group separation conditions and may overlap. High flow rates are furthermore not desirable because this does not allow for an effective separation of proteins, and the column load must be kept low in order to obtain a reasonable separation of the individual proteins. Thus gel filtration used in the fractionation mode has only been recommended for separation of proteins as a last polishing step where the volume to be fractionated is small.

During gel filtration (group separation mode), vWF is separated from the main part of the other plasma proteins. Such gel filtration may suitably be carried out by loading thawed plasma in a volume corresponding to 25% of the bed volume. The first protein peak eluting from the column is collected as this protein peak have a high content of vWF, in particular HMW-vWF-multimers. Proteins are separated on the basis of their size. Thus, this unique initial plasma fractionation step results in a protein fraction enriched in HMW-vWF-multimers in contrast to traditionally used fractionation schemes wherein the initial step is cryoprecipitation of plasma, in which procedure the proteins are separated on the basis of their solubility characteristics at a temperature of approximately 2–4° C.

The gel filtration may suitably be carried out by loading starting material, e.g. thawed plasma, in a volume corresponding to 25% of the bed volume at a gel filtration column packed with e.g. Sepharose® CL4B, Sepharose® CL2B, Sepharose® 4FF, Sepharose® 6FF, Sephacryl® S-500, Biogel® A-5m, Fractogel® HW-65, TSX® HW-40 or another gel filtration medium equilibrated in a buffer containing e.g. citrate, Tris, histidine, lysine, acetate or other common buffering substances.

The process according to the invention may further comprise one or more additional purification steps such as ion exchange chromatography, ultrafiltration, precipitations, and affinity chromatography.

Preferably, the preparation is subjected to one or more virus inactivation steps. Such virus inactivation steps are preferably carried out so as to inactivate both enveloped viruses such as HIV and hepatitis B and C, and non-enveloped viruses such as hepatitis A and human parvovirus B19. Thus, the preparation is suitably incubated with a solvent and a detergent thereby inactivating lipid-enveloped viruses as described in Ref. 12. Then solvent and detergent are subsequently removed from the solution, e.g. by means of an ion exchange step. Buffer exchange could then be performed for example by desalting. Such virus inactivation may be performed at any time during the process, but is suitably performed before or between the ion exchange steps. To inactivate non-enveloped viruses, the preparation may suitably be concentrated by ultra-filtration and then freeze-dried, and subsequently incubated for 72 hours at 80° C. as described in Ref. 13.

The invention also relates to the use of a VWF preparation as defined above for preparing a medicament for the treatment of bleeding disorders, in particular for the treatment of von Willebrand's Disease (vWD), vWD-induced haemophilia or haemophilia A.

In a further aspect, the invention relates to a pharmaceutical composition comprising as active ingredient a vWF preparation as defined above in combination with at least one pharmaceutically acceptable excipient such as albumin, amino acids and sugars.

The pharmaceutical compositions of the invention may be administered by any suitable route which leads to a concentration in the blood corresponding to which a therapeutic effect is obtained. The choice of administration route and administered amount depends i.a. on the age and weight of the patient as well as on the severity of the disease.

Pharmaceutical compositions may be formulated according to conventional pharmaceutical practice. The compositions may suitably be fluid- or liquid compositions which are suitable for parenteral administration. Examples are sterile solutions, emulsions, suspensions as well as powders, dispersible powders or granules suitable for preparing aqueous suspensions by addition of water, and they should be free from pyrogens. Such formulations may further comprise dispersing or wetting agents, suspending agent, emulsifying agents, solubility enhancing agents, and preservatives. Furthermore, the compositions may contain a suitable hydrophilic solvent such as ethanol, glycerol, propylene glycol or polyethylene glycol or a lipophilic solvent such as oil, ethyl oleate or isopropyl myristate.

The invention is further illustrated by the following non-limiting examples.

EXAMPLES

Example 1

Description of vWF-multimer Analysis for Demonstration of Multimer Pattern in vWF Preparations The multimeric structure of vWF is evaluated by agarose gel electrophoresis in the presence of SDS (sodium dodecyl sulphate). After electrophoresis, protein is transferred from the agarose gel onto nitrocellulose membranes, and vWF-protein is visualised by specific immunoenzymatic staining.

Agarose (HGT (P), Seakem 50053) gels are cast on glass plates (12 cm×12 cm, 1 mm thick). A 10.5×12 cm running gel (1.7 mm thick) is cast from a solution of 0.8% agarose in 0.375 M Tris buffer containing 0.1% SDS and adjusted to pH 9.2 (running buffer). On the remaining part of the glass plate, a 1.5×12 cm stacking gel (1.7 mm thick) is cast containing 8 wells (8×1.5 mm) that are made with a comb during casting at approx. 7 mm from the interface with the running gel. The stacking gel is prepared as a 0.6% agarose solution in 0.125 M Tris buffer containing 0.1% SDS and adjusted to pH 6.8 (stacking buffer).

Test samples are diluted with a 0.01 M Tris buffer, containing 1 mM EDTA, 2% SDS, 0.02% Bromphenol Blue (tracking dye), pH 8.0, until a concentration of 0.10–0.15 IU vWF:Ag/ml is obtained. The diluted samples are heat-treated at 60° C. for 15 minutes and then mixed with an equal volume of a 1.2% agarose solution prepared in stacking buffer and pre-warmed to 60° C. 20 µl of the mixtures are applied to separate wells in the stacking gel.

Electrophoresis is performed using a horizontal electrophoresis system and an electrophoresis buffer containing 0.04 M Tris, 0.384 M glycine, 0.1% SDS, pH 8.4–8.5. A constant current of 30 mA/gel is applied until the tracking dye reaches the running gel, at which time the current is lowered to 3 mA/gel. The electrophoresis is stopped when the tracking dye reaches the anode wicks (approx. 16 hours).

Immediately after completion of the electrophoresis, the proteins are transferred from the gel to a prewetted (overnight in a 10 mM Tris buffer containing 0.15 M NaCl, 0.15% SDS, and 20% methanol, pH 7.40) nitrocellulose filter (PVDH, cat.no. IPVH 15150, Millipore) by vacuum blotting for 90 minutes at 40 mBar (VacuGene XL Blotting System, Pharmacia Biotech, Allerod, Denmark). Transfer buffer used for blotting is a 10 mM Tris buffer containing 0.15 M NaCl and 0.15% SDS, pH 7.40.

After transfer of the proteins, free protein binding sites on the nitrocellulose filter are blocked by incubating the filter in a 10 mM Tris buffer containing 0.15 M NaCl, and 2.5% Bovine Serum Albumin, pH 7.40 (blocking buffer) for minimum 2 hours. The nitrocellulose filter is then incubated overnight with rabbit anti-human vWF (DAKO A 082, DAKO A/S, Glostrup, Denmark) at a dilution of 1 in 1000 in blocking buffer. The filter is washed three times (each 10 minutes) with washing buffer (10 mM Tris buffer containing 0.15 M NaCl and 0.05% Tween, pH 7.40) followed by incubation for 2 hours with murine anti-rabbit monoclonal antibody (DAKO M 737, DAKO A/S, Glostrup, Denmark) at a dilution of 1 in 500 in blocking buffer and another triple washing with washing buffer. Visualising of the vWF protein bands is performed using an alkaline phosphatase labelling kit (APAAP K 670, DAKO A/S, Glostrup, Denmark) and BCIP/NBT-tablets (Sigma B 5655) as substrate. The reaction is terminated by thorough washing in distilled water. The multimers are observed as bands. The first band is the protomer composed of two monomers and it has a molecular weight of approximately 500 kD, but in some preparations a band corresponding to the monomer, with a molecular weight of approximately 225 kD, can be seen.

Figure 1:
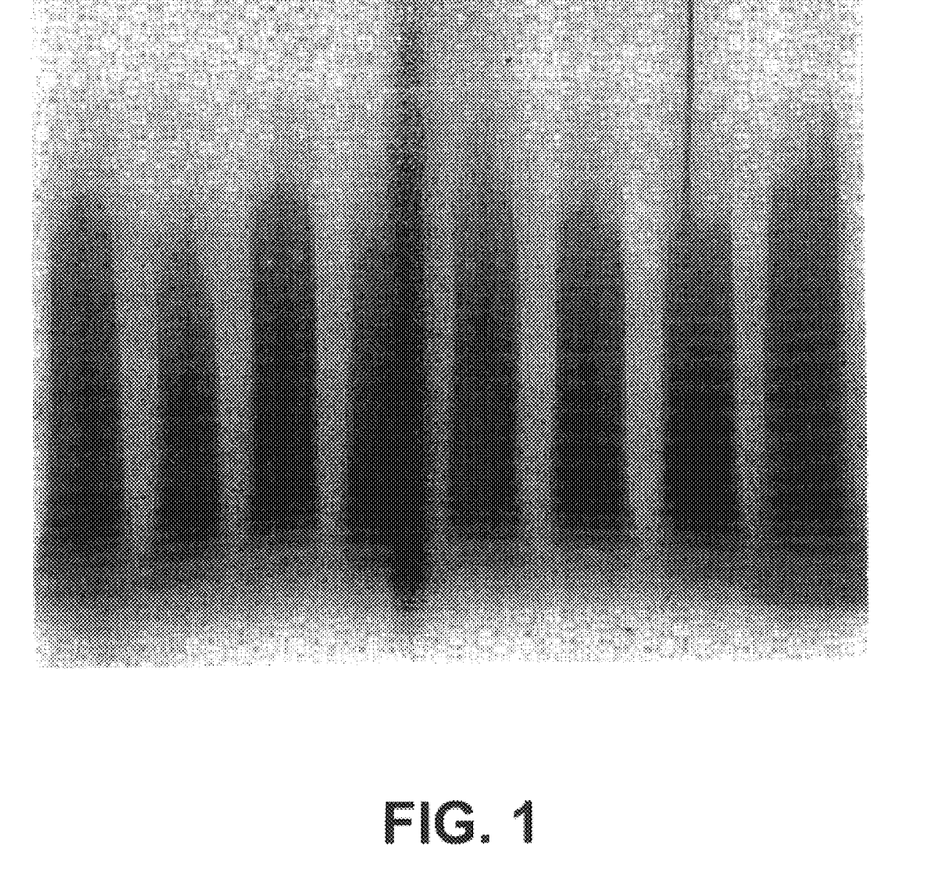
FIG. 1 shows the multimeric pattern of plasma and different vWF-containing preparations purified from plasma. The analysis was performed as described in the first part of Example 1.

FIG. 1 shows the multimeric pattern of plasma and different vWF-containing preparations purified from plasma. The multimer analysis was performed as described above.

The distribution of vWF-multimers can also be calculated after scanning of the dried nitrocellulose filter, using a Pharmacia LKB ImageMaster DTS (Pharmacia Biotech, Allerød, Denmark). The amount of low molecular multimers (LMW) vWF is calculated as the staining intensity of protein in bands corresponding to protomer numbers 1% to 6 (protomer number 1 is the protomer that has travelled farthest) in percent of the total staining intensity of all protomers in that lane. The amount of intermediate molecular weight (IMW)-multimers is likewise calculated as the staining intensity of protein in bands corresponding to protomer numbers 7% to 12. The amount of high molecular weight (HMW)-multimers is calculated as the staining intensity of proteins in all bands corresponding to multimers with more than 12 protomers in percent of the total staining intensity of all protomers in that lane.

Figure 2:
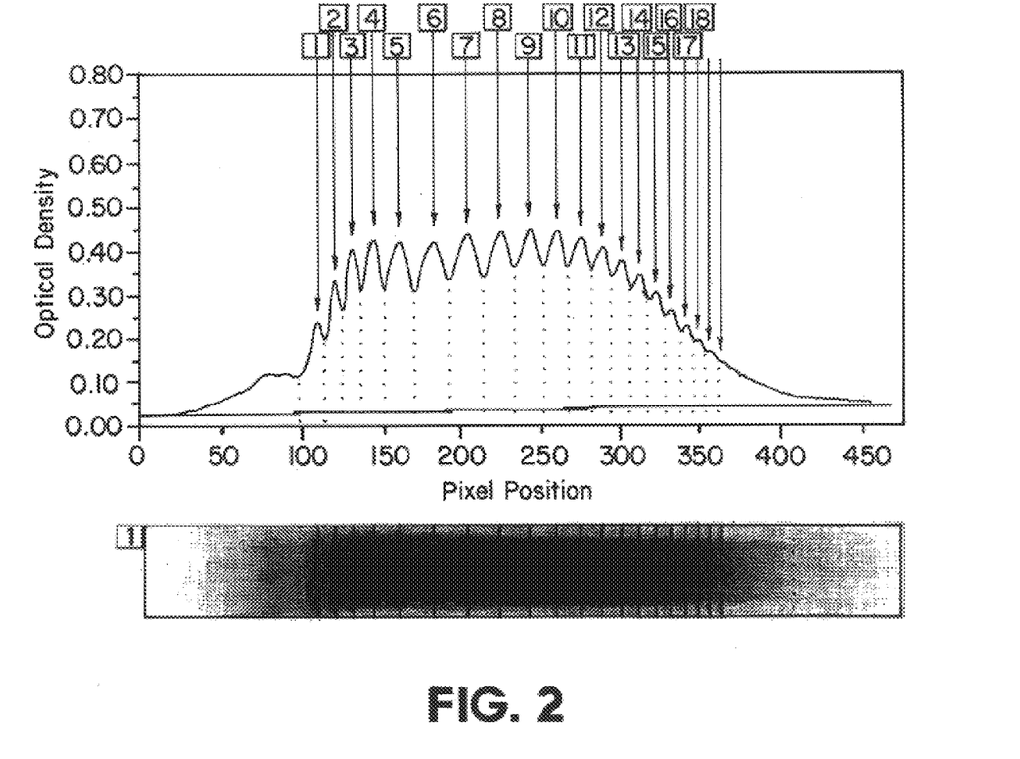
FIG. 2 shows the scanning of the multimeric pattern of a vWF-containing preparation purified from plasmapheresis plasma as described in Example 3. The multimer scanning was performed as described in the second part of Example 1.

FIG. 2 shows the scanning of the multimeric pattern of a vWF-containing preparation purified from plasmapheresis plasma as described in Example 3. The multimer scanning was performed as described above. As can be seen from the figure, the vWF-containing preparation comprises a very high content of vWF-multimers composed of 13 or more protomers (band 13 and higher).

Example 2

Description of ELISA Assays von Willebrand Factor Antigen

Maxisorp® microtitre plates (Life Technologies, Denmark) were coated with anti-human vWF (DAKO, Denmark, A082) overnight at room temperature. After washing the plates, diluted test samples and standard (an in-house plasma pool calibrated against "WHO 3rd international standard for factor VIII and von Willebrand factor in plasma", code 91/666) were applied to the plates. After incubation overnight, the plates were washed and peroxidase-conjugated anti-human vWF (DAKO, Denmark, P226) added. The plates were incubated at room temperature for four hours, then washed, whereafter a substrate for peroxidase, TMB (Kirkegaard & Perry), was added resulting in development of a colour signal, proportional to the amount of vWF in the wells. After stopping the colour development by addition of phosphoric acid, the intensity of the colour signal was measured spectrophotometrically at 450 nm using 620 nm as reference wave length.

Determination of Fibrinogen

Maxisorp® microtitre plates (Life Technologies, Denmark) were coated with rabbit anti-human fibrinogen (DAKO A080) overnight at room temperature. After washing the plates, diluted test samples and standard (Behring control plasma) were applied to the plates. After incubation overnight, the plates were washed and peroxidase-conjugated rabbit anti-human fibrinogen (DAKO, Denmark, P445) added. The plates were incubated at room temperature for six hours, then washed, whereafter a substrate for peroxidase, TMB (Kirkegaard & Perry), was added resulting in development of a colour signal, proportional to the amount of fibrinogen in the wells. After stopping the colour development by addition of phosphoric acid, the intensity of the colour signal was measured spectrophotometrically at 450 nm using 620 nm as reference wave length.

Determination of Fibronectin

Maxisorp® microtitre plates (Life Technologies, Denmark) were coated with rabbit anti-human fibronectin (DAKO, Denmark, A245) overnight at room temperature. After washing the plates, diluted test samples and standard (Behring plasma protein standard) were applied to the plates. After incubation for three hours, the plates were washed and peroxidase-conjugated rabbit anti-human fibronectin (DAKO, Denmark, P246) added. The plates were incubated at room temperature for four hours, then washed, whereafter a substrate for peroxidase, TMB (Kirkegaard & Perry), was added resulting in development of a colour signal, proportional to the amount of fibronectin in the wells. After stopping the colour development by addition of phosphoric acid, the intensity of the colour signal was measured spectrophotometrically at 450 nm using 620 nm as reference wave length.

Determination of VWF:CBA

CovaLink microtitreplates (Life Technologies, Denmark) were coated overnight with collagen type III (Southern Biotechnology no. 1230-01S). After washing the plates, diluted test samples and standard (an in-house vWF-preparation calibrated against "WHO 3rd international standard for factor VIII and von Willebrand factor in plasma", code 91/666, defining the amount of vWF collagen-binding activity in the WHO-standard as identical with the stated content of vWF:RCo) were applied to the plates. After incubation for one hour, the plates were washed and peroxidase-conjugated anti-human vWF (DAKO P226) added. The plates were incubated at room temperature for one hour, then washed, whereafter a substrate for peroxidase, TMB (Kirkegaard & Perry), was added resulting in development of a colour signal, proportional to the amount of vWF bound to collagen in the wells. After stopping the colour development by addition of phosphoric acid, the intensity of the colour signal was measured spectrophotometrically at 450 nm using 620 nm as reference wave length.

Example 3

Approximately 700 kg plasma was thawed and 1 IU heparin/ml plasma was added. vWF was separated from the main part of the other plasma proteins by means of gel filtrations of plasma sub-pools with approximate volumes of 175 liter each at a column packed with approx. 700 liter Sepharose® 4 FF (Pharmacia, Denmark) using a "chromatography buffer" with the following composition: 20 mM Na-citrate, 2.55 mM $CaCl_2$, 0.15 M NaCl, pH 7.0. The eluates were pooled, and 0.1% Tween® 80 was added.

The pool was loaded to a column packed with 23 liter Q-Sepharose® HP anion-exchange gel equilibrated in the above-mentioned "chromatography buffer" with 0.1% Tween® 80 added. After washing-out non-bound proteins from the gel matrix using the "chromatography buffer" with 0.1% Tween® 80 added, vWF was eluted (and thereby concentrated) with the following buffer: 20 mM Na-citrate, 2.55 mM $CaCl_2$, 1.0 M NaCl, 12% glycerol, 1.0 IU heparin/ml, 0.1% Tween® 80, pH 6.0.

The eluate was formulated with 1.0% Tween® 80 and 0.3% TNBP and left with slow stirring for 6 hours at 24° C. thereby securing inactivation of lipid-enveloped viruses (first virus inactivation step).

After termination of the virus inactivation step, the solution was diluted with a buffer consisting of 10 mM histidine, 1.9 mM $CaCl_2$, pH 7.0% to a final conductivity of 15 mS/cm. The diluted solution was loaded to a column packed with 3 liter SP-Sepharose® HP cation-exchange gel (Pharmacia, Denmark) equilibrated with "chromatography buffer" at pH 6.7. This buffer was also used for washing-out un-bound proteins before eluting vWF with a buffer consisting of: 10 mM histidine, 0.2 M $CaCl_2$, 0.27 M NaCl, pH 7.0.

The eluate was desalted using a column packed with 27 liter Superose 12 (Pharmacia, Denmark) into a buffer consisting of 10 mM histidine, 1.5% mannitol, 0.5% sucrose, pH 7.1.

The desalted eluate was concentrated by means of ultra-filtration. Before performing the ultra-filtration, human serum albumin was added corresponding to a final concentration after ultra-filtration of 0.25% . After sterile filtration, the solution was dispensed in a volume corresponding to 500 U vWF collagen binding activity (vWF:CBA, see table 2 legend b) in each vial. The solution was freeze-dried.

The freeze-dried preparation was heat-treated at 8° C. for 72 hours (second virus inactivation step).

Example 4

Three batches of VWF-preparation were prepared as described in Example 3. The three preparations(designated HS-VWF plus a number) were analysed with regard to vWF:Ag and total protein content before addition of the stabiliser albumin. The specific activity [IU vWF:Ag per mg of total protein] was calculated. The results appear from Table 1.

TABLE 1

Specific activities of three batches of HS-vWF before addition of albumin.

| | HS-vWF 726540 | HS-vWF 727140 | HS-vWF 728540 |
|---|---|---|---|
| vWF:Ag [IU/ml][a] | 22.6 | 14.1 | 20.7 |
| Total protein[b] [mg/ml] | 0.145 | 0.136 | 0.123 |
| Specific activity [IU vWF:Ag/mg protein] | 156 | 104 | 168 |

[a]vWF:Ag designate the amount of von Willebrand factor antigen present; vWF:Ag was measured as described in Example 2.
[b]Total protein content was determined using the Bradford assay (according to standard procedures) using human serum albumin as standard.

Example 5

The three vWF preparations described in Example 4 were analysed with respect to the haemostatic quality of vWF present. The results were compared with results for three commercially available vWF-containing FVIII-preparations (Alphanate from Alpha Therapeutic, United Kingdom (designated A), 8Y from BPL, United Kingdom (designated B) and Haemate from Centeon, Germany (designated C)) using the same method of analysis. Furthermore, the contents of the cold-insoluble proteins fibrinogen and fibronectin were quantitated in HS-VWF preparations and the commercially available vWF-containing FVIII-preparations. The results are shown in Table 2.

TABLE 2

Characteristics of the three HS-vWF preparations and the commercially available vWF-containing FVIII-preparations as well as vWF-multimeric distribution in a pool of normal human plasma.

| | HS-vWF 726540 | HS-vWF 727140 | HS-vWF 728540 | Plasma pool |
|---|---|---|---|---|
| vWF:Ag[a] [IU/vial] | 653 | 470 | 483 | |
| vWF:CBA[b] [U/vial] | 492 | 471 | 395 | |
| Multimers[c] | | | | |
| % HMW-vWF | 19 | 20 | 20 | 21 |
| % IMW-vWF | 42 | 44 | 41 | 40 |
| % LMW-vWF | 39 | 36 | 39 | 39 |
| FVIII[d] [IU/vial] | 510 | 462 | 293 | |
| Fibrinogen[e] [ng/IU vWF:Ag] | 34 | 26 | 20 | |
| Fibronectin[f] [ng/IU vWF:Ag] | 51 | 30 | 26 | |

| | A | B | C | Plasma pool |
|---|---|---|---|---|
| vWF:Ag[a] [IU/vial] | 602 | 1270 | 1144 | |
| vWF:CBA[b] [U/vial] | 467 | 836 | 1229 | |
| Multimers[c] | | | | |
| % HMW-vWF | 12 | 12 | 14 | 21 |
| % IMW-vWF | 41 | 39 | 45 | 40 |
| % LMW-vWF | 47 | 49 | 41 | 39 |
| FVIII[d] [IU/vial] | 603 | 489 | 467 | |
| Fibrinogen[e] [ng/IU vWF:Ag] | 673 | 67,246 | 1,162 | |
| Fibronectin[f] [ng/IU vWF:Ag] | 1,620 | 5,190 | 421 | |

[a]vWF:Ag designate the amount of von Willebrand factor antigen present; vWF:Ag was measured by an ELISA assay as described in Example 2.
[b]vWF:CBA = von Willebrand factor collagen binding activity, which is an assessment of how much activity the von Willebrand factor protein possesses, was measured by an ELISA assay as described in Example 2.
[c]The von Willebrand factor multimer distribution was analysed according to the method described above in Example 1.
[d]The factor VIII activity was measured by a two-stage chromogenic assay (Coamatic Factor VIII analysis kit by Chromogenix) using Nordiate (FVIII, HemaSure) calibrated against "5th International Standard for Blood Coagulation Factor VIII) as standard.
[e]Fibrinogen was measured as described in Example 2.
[f]Fibronectin was measured as described in Example 2.

As seen from table 2, only the vWF-preparations according to the invention had an almost intact vWF multimeric pattern and a high purity of vWF relative to fibrinogen and fibronectin content.

Example 6

HS-vWF batch no. 728540 was prepared as described in Example 3. Samples of intermediate products were drawn during fractionation. In these samples, fibrinogen and fibronectin were determined. The results appear from Table 3. Fibrinogen and fibronectin were determined as described in Example 2.

TABLE 3

Characteristics of intermediate products drawn during fractionation of HS-vWF batch no. 728540.

| | ng fibrinogen/ IU vWF:Ag | ng fibronectin/ IU vWF:Ag |
|---|---|---|
| Plasma | 1,266,667 | 179,852 |
| Eluate from gel filtration column | 25,813 | 2,417 |
| Eluate from 1st ion exchanger | 8,419 | 2,175 |
| Desalted eluate from 2nd ion exchanger | 24 | 15 |
| Final preparation | 20 | 26 |

As calculated from table 3, fibrinogen was reduced approx. 63,000 times and fibronectin approx. 7,000 times compared to vWF:Ag during purification of HS-vWF batch 728540. The content of fibrinogen was reduced in all steps from plasma to desalted eluate, whereas the fibronectin content was reduced at the gel filtration and 2nd ion exchange steps with no appreciable reduction at the 1st ion exchange step. Thus, it can be concluded that the two ion exchange steps contribute to the purity of the vWF-preparation in different manners.

References

1. Rodeghiero et al., Vox Sang. 62, 193–199 (1992)
2. Haemostasis 24, 285–288, 1994 and Blood 83(10), 3018–3027 (1994)
3. Haemostasis 24, 285–288 (1994)
4. Blood 83(10), 3018–3027 (1994)
5. EP 469 985 B1 (Association D'Aquitaine pour le Developpement de la Transfusion Sanguine et des Recherches Hematologiques)

6. WO 91/07438 A1 (Novo Nordisk A/S)
7. EP 705 846 A1 (Immuno AG)
8. WO 96/10584 A1 (Immuno AG)
9. WO 97/34930 A1 (Immuno AG)
10. Ruggeri and Ware, FASEB J. 7, 308–316, 1993
11. Ruggeri and Zimmermann, Blood 57(6), 1140–1143, 1981
12. Prince et al. The Lancet, 706–710, Mar. 29 (1986)
13. Hart et al. Vox Sanguinis 67, 345–350 (1994).

What is claimed is:

1. A preparation comprising high-purity von Willebrand Factor (vWF) and multimers thereof wherein at least 15% of the total number of said multimers are multimers which contain 13 or more protomers, and wherein the total amount of fibrinogen and fibronectin is less than 1500 ng per International Unit of vWF present in the preparation.

2. The preparation according to claim 1 wherein at least 18% of the total number of said multimers contain 13 or more protomers.

3. The preparation according to claim 1, wherein the amount of fibrinogen is less than 500 ng/IU vWF.

4. The preparation according to claim 1, wherein the amount of fibronectin is less than 500 ng/IU vWF.

5. The preparation according to claim 1, wherein the amount of fibronectin is less than 200 ng/IU vWF.

6. The preparation according to claim 1, comprising more than 0.1 IU FVIII procoagulant activity (FVIII:C)/IU vWF.

7. The preparation according to claim 1, comprising more than 0.2 IU FVIII procoagulant activity (FVIII:C)/IU vWF.

8. The preparation according to claim 1, purified from human plasma.

9. A composition comprising as active ingredient the preparation according to claim 1 in combination with at least one pharmaceutically acceptable excipient.

* * * * *